United States Patent [19]

Heuscher

[11] Patent Number: 5,276,614
[45] Date of Patent: Jan. 4, 1994

[54] DYNAMIC BANDWIDTH RECONSTRUCTION

[75] Inventor: Dominic J. Heuscher, Aurora, Ohio

[73] Assignee: Picker International, Inc., Highland Hts., Ohio

[21] Appl. No.: 438,687

[22] Filed: Nov. 17, 1989

[51] Int. Cl.⁵ .............................................. G06F 15/00
[52] U.S. Cl. ................................................ 364/413.16
[58] Field of Search ....................... 364/413.16, 413.21, 364/413.23, 413.14, 724.05; 382/54, 6; 358/111

[56] References Cited

U.S. PATENT DOCUMENTS

| 4,288,695 | 9/1981 | Walters et al. | 378/5 |
| 4,305,127 | 12/1981 | Heuscher | 364/414 |
| 4,333,145 | 6/1982 | Heuscher et al. | 364/414 |
| 4,707,786 | 11/1987 | Dehner | 364/413.21 |
| 4,712,178 | 12/1987 | Tuy et al. | 364/413.19 |
| 4,714,997 | 12/1987 | Crawford et al. | 364/414 |
| 4,716,368 | 12/1987 | Haacke | 324/309 |
| 4,761,819 | 8/1988 | Denison et al. | 382/54 |
| 4,792,900 | 12/1988 | Sones et al. | 364/413.23 |
| 4,887,306 | 12/1989 | Hwang et al. | 382/54 |
| 4,979,111 | 12/1990 | Nishimura | 364/413.16 |
| 5,065,444 | 11/1991 | Garber | 382/54 |

FOREIGN PATENT DOCUMENTS 0242909 7/1986 European Pat. Off.
2547149 9/1987 France .

OTHER PUBLICATIONS

Convolution Algorithms for Arbitrary Projection Angles by Mark E. Davison and F. A. Grünbaum, IEEE TRans. on Nuc. Sci., vol. NS-26, No. 2, Apr. 1979.

Primary Examiner—Roy N. Envall, Jr.
Assistant Examiner—Xuong Chung
Attorney, Agent, or Firm—Fay, Sharpe, Beall, Fagan, Minnich & McKee

[57] ABSTRACT

A scanner (A), such as a CT or MR scanner, non-invasively examines a region of interest of subject and generates a plurality of views indicative thereof which are reconstructible into an image representation. A filter control (14) generates a bandwidth scaling factor ($BWF_\theta$) and a bandwidth offset (BWO) for each view. Preferably, the selected bandwidth scaling factor is the maximum of a plurality of bandwidth scaling factors based on different criteria including noise, missing views, material surrounding the region of interest, or noise texture. The bandwidth scaling factor is then used to address a filter curve look up table (18) to select from a plurality ($N_T$) of filter values. The digital filter values are interpolated (20) or extrapolated as necessary to match the number of values ($N_S$) in each sampled view. The digital filter values and the view values are multiplied (22) point by point to create filtered views which are reconstructed (30) into the image representation for storage in an image memory (32) or displayed on a video monitor (34).

14 Claims, 3 Drawing Sheets

DYNAMIC BANDWIDTH RECONSTRUCTION

BACKGROUND OF THE INVENTION

The present invention relates to the art of image reconstruction. It finds particular application in conjunction with CT scanners and will be described with particular reference thereto. However, it is to be appreciated that the present invention is also applicable to the reconstruction of images from magnetic resonance data, digital x-ray data, PET data, and the like.

A CT scanner generates lines or views of image data values. The data values of each view commonly represent radiation attenuation along rays of a fan shaped swatch through a slice of a patient. Different views represent the same fan shaped swatch but at different angular orientations about the patient. The views of data are collected in a data memory and reconstructed into an image representation, most commonly by a process of convolution and backprojection, also known as filtered backprojection. By filtering all the views with a common filter, image artifacts, noise degradation, and the like can be reduced or eliminated. Conventionally, all views are filtered with the same filter function.

In U.S. Pat. No. 4,333,145, only some data is filtered prior to the reconstruction. The data collected from rays which pass through the patient's arm pass through more bone than other rays giving that data a different bandwidth. The '145 patent filters only the rays of data that pass through the patient's arms with a preselected fixed filter function to reduce or eliminate bandwidth related artifacts in the resultant image.

Data from other scanners has also been filtered either as the data is collected or reconstructed into an image representation. However, such filtering again tends to be fixed for a given image.

The present invention contemplates a new and improved filtering technique which overcomes the above referenced problems and others.

SUMMARY OF THE INVENTION

In accordance with one aspect of the present invention, a scanner generates data views for reconstruction into an image representation. A filter means filters each of the views with one of a range of filter functions. A filter control means selects among the range of filter functions on a view-by-view basis. A reconstruction means reconstructs an image representation from the filtered views.

In accordance with another aspect of the present invention, the filter control means includes an adaptive filter means for selecting a view dependent filter function such as on the basis of one or more of: the noise of each view, missing views, material adjacent the region of interest, and a noise texture filter function. A comparing means compares filter functions selected on two or more of these bases with preselected criteria and controls the filter means in accordance with a selected one of the filter functions. In the preferred embodiment, the comparison criteria is based upon the filter function which provides the most filtering.

In accordance with another aspect of the present invention, a method of generating image representations is provided. A plurality of views of data are generated for reconstruction into an image representation. Each view is filtered with a filter function. A filter function is selected for each view which provides optimal filtering for each view. The uniquely filtered views are reconstructed into the image representation (e.g. two dimensional uniformity).

In accordance with a more limited aspect of the present invention, the filter controlling criteria is based on noise equalization, bandwidth correction for missing views, known system or image constraints, or noise texture.

In accordance with a still more limited aspect of the present invention, filter functions for a plurality of corrections are determined and the filter function which provides the greatest filtering is selected.

One advantage of the present invention is that it optimizes the filter function for each of the multiplicity of views of a reconstructed image.

Another advantage of the present invention is that it reduces artifacts in the resultant image.

Still further advantages of the present invention will become apparent to those of ordinary skill in the art upon reading and understanding the following detailed description.

BRIEF DESCRIPTION OF THE DRAWINGS

The invention may take form in various parts and arrangements of parts or in various steps and arrangements of steps. The drawings are only for purposes of illustration and are not to be construed as limiting the invention.

DETAILED DESCRIPTION OF THE PREFERRED EMBODIMENT

Figure 1A:
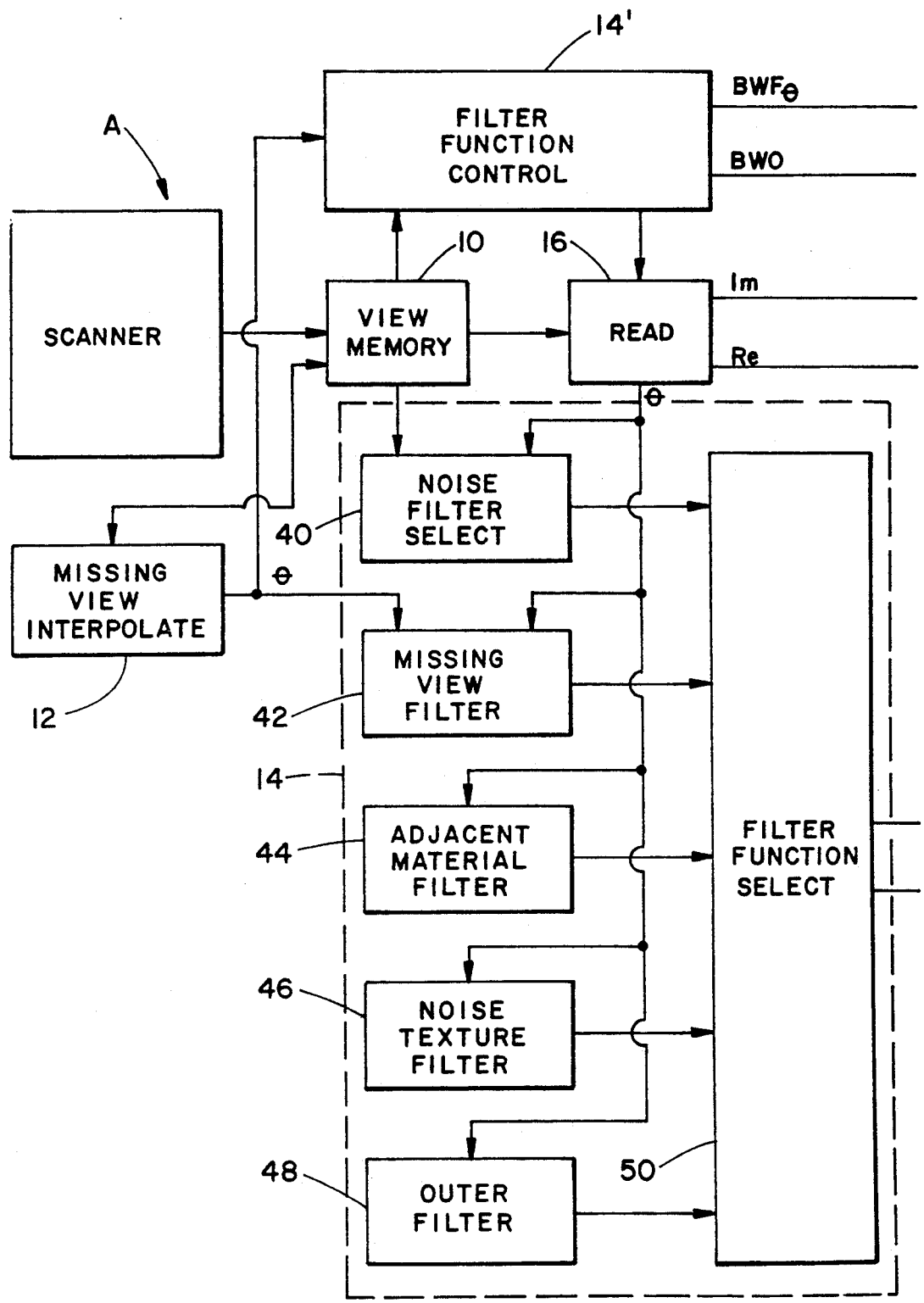
FIGS. 1A and 1B taken together are a diagrammatic illustration of the present invention.
Figure 1B:
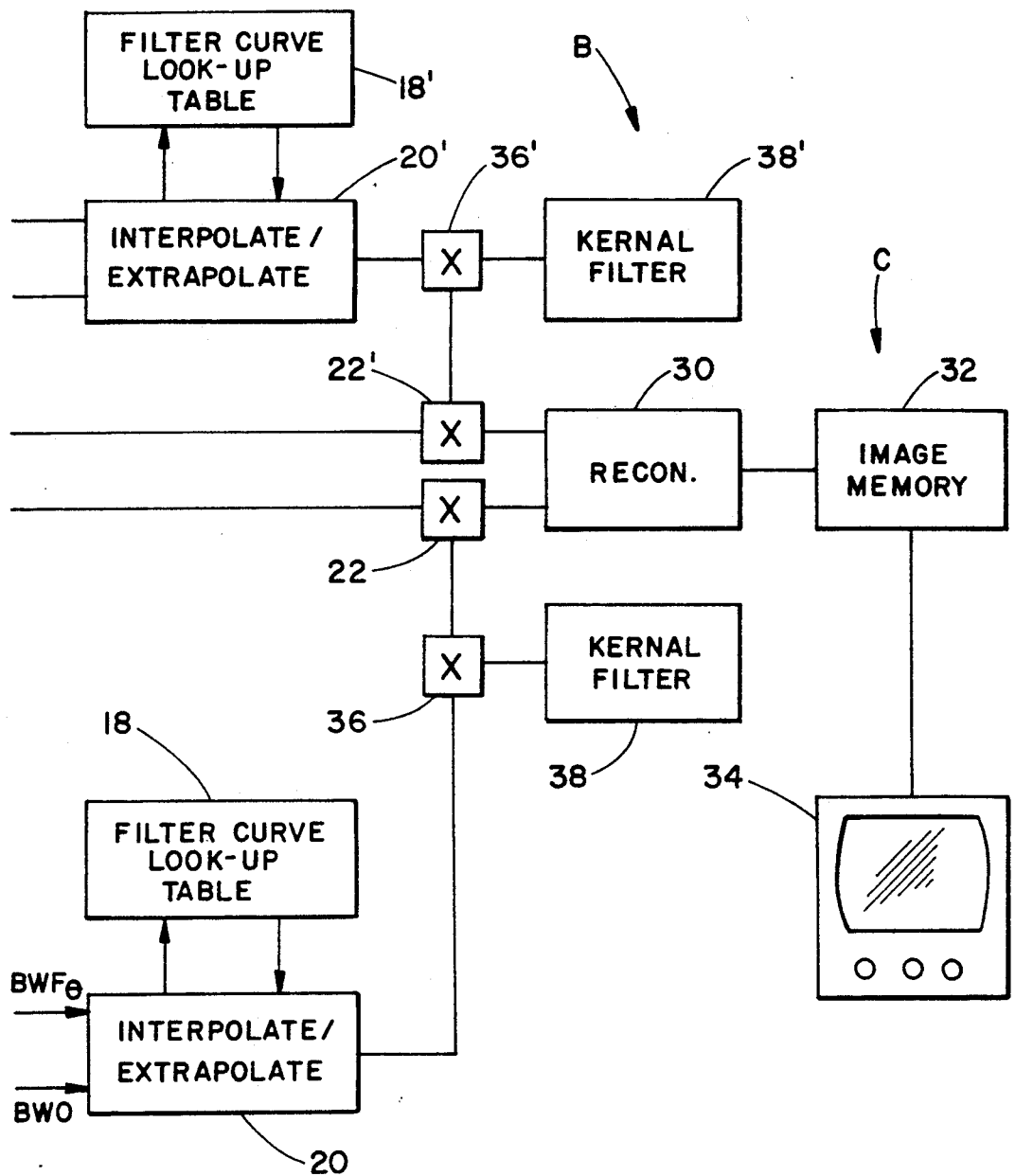

A scanner A such as a CT scanner, magnetic resonance scanner, PET scanner, digital x-ray scanner, or the like non-invasively examines a region of interest, e.g. a slice or volume, of a subject in an examination region. The scanner generates views of data, each view indicative of a property of the region of interest and identifications of each view. In a third generation CT scanner, each view is a series of data values that correspond to an arc of radiation detectors which rotate about a scan circle with a radiation source. The detectors are resampled each time the source and detectors rotate an incremental angular distance to produce additional views of data. In a magnetic resonance scanner, each view includes data values corresponding to each of a spectrum of frequencies sampled with one of a plurality of phase encodings. The data generation is repeated with each of the phase encodings to generate the plurality of views. In a fourth generation scanner, radiation detectors are mounted stationarily around the scan circle. Each detector is sampled a multiplicity of times as the x-ray source rotates around the scan circle from the detector. Each view corresponds to the samplings of a single detector as the radiation source rotates behind the scan circle. Each of the multiplicity of detectors provides one of the plurality of views.

A filter means B selects and filters each view with a corresponding filter function to compensate for one or more of noise, missing views, high density objects, noise texture, or the like. An image reconstruction means C reconstructs the uniquely filtered views into an image representation.

Looking more specifically to the filter means B, the data is stored in a view memory means 10 in accordance with the view designations. A missing data interpolating means 12 interpolates adjacent data to replace the data of any missing views or other missing data. The interpolated data is returned to the view memory 10 to fill the memory cells left empty by the missing data. The interpolating means 12 also provides an indication of the interpolated views or other interpolated data to a filter control means 14.

A read out means 16 serially reads each view of $N_\theta$ sampled views from the view memory 10. Alternately, the memory 10 may be a buffer or the like through which the views pass serially for pipeline processing. As each view is read out, the filter control means 14 designates a corresponding filter function for filtering the read view. More specifically to the preferred embodiment, the filter control means generates a bandwidth scaling factor $BWF_\theta$ or other filter designation which addresses a filter function or curve look up table 18 which stores a digital description of each of a range of selectable filter functions or curves. The filter functions 20 include a notch filter, low pass filter, high pass filter, band pass filter, or the like. Preferably, these filters are based on cosine functions. Various other filter functions may, of course, also be utilized.

The filter table 18 stores a limited number of points or values $N_T$ of the filter curve. An interpolating means 20 interpolates between the stored filter points, e.g. a linear interpolation, to expand the filter function to as many values as the number of data values of the sampled views $N_S$. A multiplying means 22 multiplies each filter function point by point with the corresponding view. When the read out means 16 reads out the next view, the filter function control means 14 determines the appropriate bandwidth scaling factor for that view and addresses the filter look up table 18. In this manner, the filter function is automatically selected individually for each view.

Commonly, each view includes real and imaginary components, also called sine and cosine or in-phase and out-of-phase components. The read out means 16 reads out the two data components for each view individually. The first filter control means 14 determines the appropriate filter for the real component and a second filter control means 14' determines the appropriate filter for the imaginary component. A second filter selection means 14' selects a second bandwidth scaling factor which accesses a second filter curve table 18' to retrieve the values of the selected filter curve. A second interpolating means 22' interpolate the filter curve to $N_S$ values such that a second multiplying means 24 can multiply each of the $N_S$ data values by a corresponding filter value.

The image reconstruction means C includes a reconstruction algorithm 30. For CT scanners, a conventional convolution and backprojection or filter backprojection algorithm may be utilized. For magnetic resonance imagers, an inverse two dimensional Fourier transform algorithm is commonly utilized. Other conventional reconstruction algorithms may be selected in accordance with the type of scanner and the nature of the diagnostic procedure. The reconstruction means accumulates the reconstructed data in an image memory 32 until all the views have been processed to form a complete electronic image representation. Each image representation may be selectively read from the image memory and displayed on a video monitor 34. Various post processing techniques may be utilized to improve the quality of the image in the image memory 32. The enhanced or raw image representations may also be stored on tape or disk, subject to other processing, or the like.

In filtered backprojection, the views of data are operated upon with a filter function. Part of this filtering operation may be incorporated in the filtering means B. The reconstruction filter may in whole or in part be combined with the filter curves stored in the filter curve look up table 18 such that the point by point multiplying means 22, 22' perform part of the reconstruction algorithm. Optionally, a multiplying means 36 may multiply the interpolated or extrapolated filter function 20 by a system kernal 38. Analogous filter-like portions of other reconstruction algorithms may also be shifted from reconstruction means C to filter means B.

In the preferred embodiment, the filter control means 14, 14' select the filter function for each view based on several criteria. Because filter control means 14 and 14' are of substantially identical construction, filter control means 14 is described in detail herein below and is to be appreciated that the description applies analogously to both. The filter control means includes an adaptive noise equalization filter selecting means 40 for selecting an appropriate filter function in accordance with the noise of each processed view. The noise may be assessed based on the noise of the preceding view, noise from a corresponding view of a preceding slice or scan, or the like. Alternately, the entire set of view data may be collected in view memory 10 before further processing is commenced such that the noise filter selecting means selects the noise filter based on the actual noise of the scan and each view.

A missing views bandwidth correction filter means 42 selects an appropriate filter for adjacent views that have been created by interpolation. That is, interpolated views have a lower bandwidth than actually collected views and may have additional noise from one of the interpolated views. The missing view bandwidth correction filter selection means 42 selects a bandwidth scaling factor that retrieves a larger, narrower bandwidth filter for the interpolated view. The bandwidth scaling factor selected for adjoining views also retrieves filter functions with a reduced bandwidth, but less reduced than for the missing view.

A predefined bandwidth correction means 44 selects a bandwidth scaling factor to compensate for high density objects or other materials adjacent the region of interest. The filter may be selected in accordance with the angular position of a CT scan view as in U.S. Pat. No. 4,333,145, may be based on data derived from the view memory 10, information from an unfiltered pilot reconstruction, or the like.

A noise texture filter means 46 selects bandwidth scaling factors which address filter functions which varies with angular position around the scan circle to provide a noise texture that is more desirable. More specifically, reconstructions based on a circularly symmetric 2-D kernel tend to have circularly symmetric noise texture which can be disconcerting. The noise texture filter selection means selects appropriate angularly dependent filter functions to stretch the noise texture at the corners into a closer approximation of a square or rectangular display.

Additional filter function selection means 48 may also be provided for selecting a filter function based on other criteria. A selection means 50 compares each of the bandwidth scaling factors designated by the filter function selection means 40-48 with preselected criteria and passes one of them as the address to the filter look-up table 18. In the preferred embodiment, the filter curve comparing means 50 selects the maximum filter function for each view, i.e. passes the smallest bandwidth.

Figure 2:
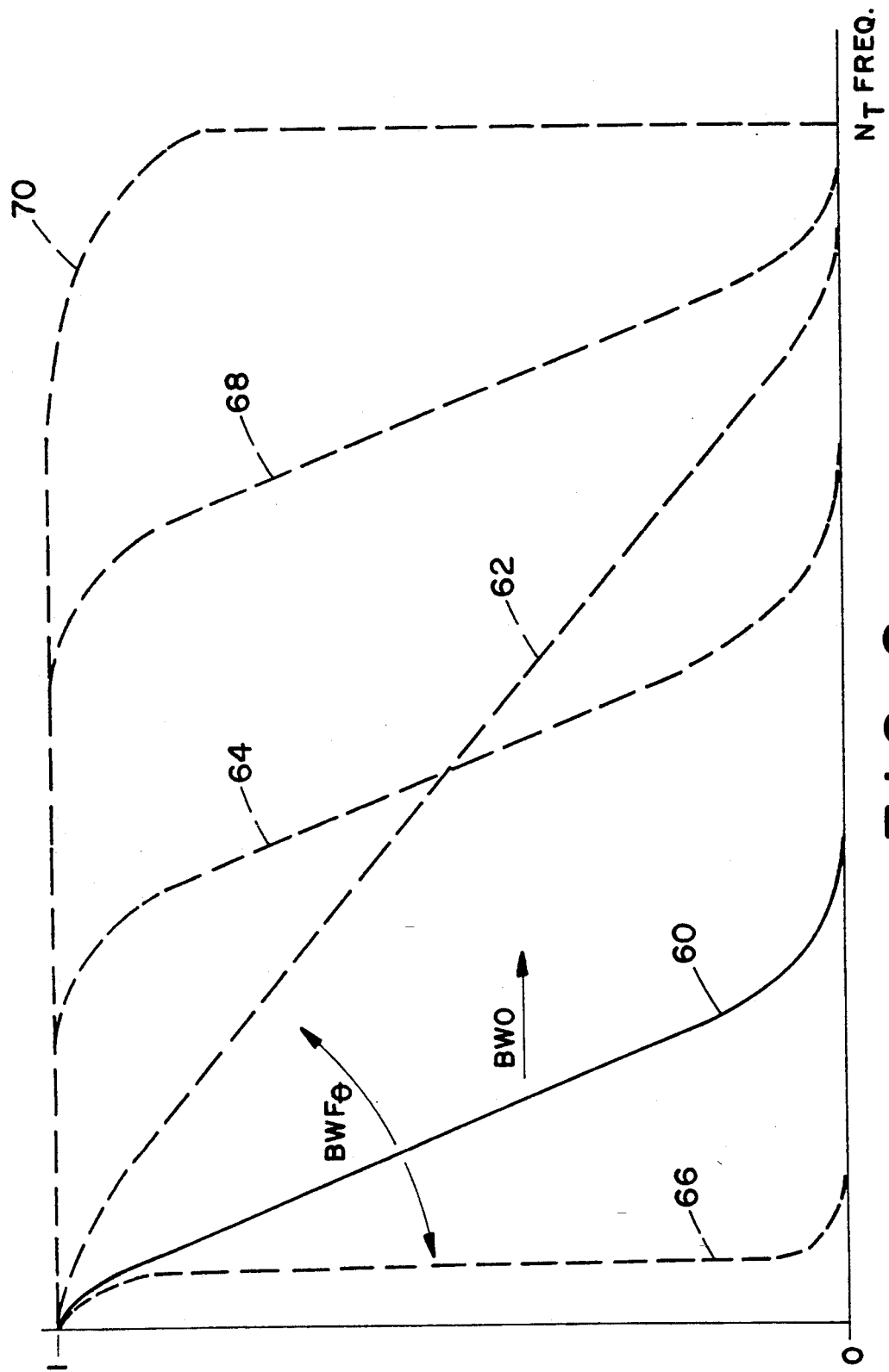
FIG. 2 illustrates a range of filter function adjustments for an exemplary low pass filter function.

With reference to FIG. 2, a typical low pass filter function 60 is illustrated. The shape of this curve is adjusted as illustrated at 62 to adjust the frequency range over which the function is applied. Curve 62 has a different slope than filter curve 60 and therefore a wide bandwidth. In addition to rescaling the filter function, the filter function may also be shifted by an offset as illustrated by filter curve 64. Filter curve 64 is essentially the same as curve 60 but shifted to cut off a smaller range of frequencies. With these two control factors, the filter function can be varied over a wide range such as the very narrow frequency range of filter curve 66 or the almost all inclusive frequency range of filter curves 68 and 70.

The look-up table 18 defines the shape of the band limiting filter function to be used in the frequency or Fourier domain, i.e. before reconstruction. The filter function control means 14 selects a bandwidth scale factor $BWF_\theta$ which defines the frequency range over which the filter function is to be applied and a bandwidth offset BWO which defines a center or other characteristic frequency of the selected filter function. The bandwidth scale factor varies from a value of zero corresponding to no band limiting, i.e. all values for the apodized function become mapped into the DC value, to an arbitrarily large factor corresponding to extreme low pass filtering to a filter value where only DC or an averaged data value is passed. Expressed mathematically, the apodized function is expressed as:

$$A_\theta(f) = T_f(O) \text{ for } BWF_\theta = 0 \qquad (1a)$$

$$A_\theta(f) = T_f(f \cdot BWF_\theta) \text{ for } 0 \leq f < N_T/BWF_\theta \qquad (1b)$$

$$A_\theta(f) = T_f(N_T) \text{ for } f \geq N_T/BWF_\theta \qquad (1c),$$

where:
$T_f(O)$ is the value interpolated by the interpolating means 20 from the bandwidth table 18 which contains $N_T+1$ values;
$BWF_\theta$ is the bandwidth scale factor as a function of the view designation $\theta$;
for sampled, real functions, f assumes the values of f=0, $\Delta f, 2\Delta f, \ldots f_N$, where $\Delta f = f_N/N_S$;
$f_N$ is the nyquist frequency of the sampled function whose spectrum is computed with a $2N_S$ sample (real) discrete Fourier transform.

The bandwidth factor $BWF_\theta$ is defined as a function of $\theta$ which in computed tomography is the projection angle. The bandwidth or resolution can be varied as a continuous function of the projection angle $\theta$. In CT, the bandwidth is sampled over $N_\theta$ discrete views. In a fourth generation CT scanner, the number of views corresponds to the number of detectors. In a third generation system, the number of views is determined by the number of x-ray source positions at which the detectors are sampled. In the CT scanner embodiment, the convolution-backprojection reconstruction performed by the reconstruction means 30 can be expressed mathematically as:

$$ALG_\theta(f) = ALG_p(f) \cdot A_\theta(f) \qquad (2)$$

where $f=0, \Delta f, 2\Delta f, \ldots f_N$; and, $ALG_p$ is the predefined system convolution kernel for convolution-backprojection. When no non-linear phase corrections are performed, these are real functions and are used to multiply the complex Fourier data in performing a Fourier convolution:

$$CD_\theta(f) = D_\theta(f) \cdot ALG_\theta(f) \qquad (3a)$$

$$= D_\theta(f) \cdot [ALG_p(f) \cdot A_\theta(f)] \qquad (3b),$$

where $D_\theta(f)$ is the Fourier transform of the projection at angle $\theta$; $ALG_\theta(f)$ is the algorithm to be applied at angle $\theta$; and $CD_\theta(f)$ is the Fourier transform of the convolved projection at angle $\theta$. Because $D_\theta$ is complex, the result $CD_\theta(f)$ is also complex. In this manner, $ALG_\theta(f)$ is defined by a single bandwidth scale factor $BWF_\theta$ which enables the above discussed view angle dependent corrections of selecting means 40, 42, 44, and 46 to be incorporated concurrently into a CT reconstruction.

In order to combine the bandwidth filter generation with the reconstruction kernel, the algorithm in look up table 18 is divided into two classes. In the first class (for $\Delta f^*BWF_\theta < 1$), the output values $A_\theta(f)$ are generated by a linear progression for each new table value read in. This results in a very efficient inner loop. The second class (for $\Delta f^*BWF_\theta \geq 1$), most values are generated by extrapolating points $T(N_T)$ for values corresponding to points beyond the limit $N_T$ of the table. Extrapolation becomes necessary because the number of points in the table $N_T$ is preferably significantly smaller than the number of sampled data points $N_S$. The points within the scope of the table, as discussed above, are generated by linear interpolation. It might be noted that when the multiplications of Equation (2) and (3b) are performed while generating the interpolation and/or extrapolation values, the amount of time added for the view dependent filtering becomes negligible, i.e. there is virtually no cost in reconstruction time.

The bandwidth offset defines the center, cut-off, or other characteristic frequency of the selected filter function. In the preferred embodiment, the selected filter function with the $BWF_\theta$ scaling factor has a preselected cut-off frequency. The filter selecting means may also designate an offset frequency, BWO, which is added or subtracted from the preselected frequency to shift the bandwidth of the filter function.

Looking now in greater detail to the adaptive noise equalization bandwidth scale factor selecting means 40, adaptive noise equalization provides for a uniform distribution of noise statistics in a reconstructed object, even substantially asymmetric objects. In many applications, it is advantageous, for good low contrast detectability, to obtain uniform noise statistics throughout the object. To accomplish this with the dynamic bandwidth algorithm described above, a bandwidth scale factor is generated which corrects for the nominal variation in noise as a function of projection angle. It is to be appreciated that the noise statistics in CT are principally based on x-ray-photon statistics.

The bandwidth factor is related to the power spectrum or noise factor by the relationship:

$$\text{Noise factor}_{BW} \simeq 1/[BWF(\theta)^* N_S/N_T + 1] \qquad (4).$$

In CT, the noise power spectrum is proportional to the prelogarithmic attenuation. From the sampled data, an estimate $A_m(\theta)$ of the maximum attenuation at angle $\theta$ is obtained for all $\theta$. $A_o$ then represents the minimum value of all $A_m(\theta)$. That is:

$$\text{Noise factor}_A \approx e^{(A_m(\theta) - A_o)} \qquad (5).$$

For the bandwidth correction factor to adjust for the attenuation noise factor, $$\text{Noise factor}_A \cdot \text{Noise factor}_{BW} \approx 1 = \text{unity noise factor} \qquad (6).$$

Thus, the noise filter selection means 40 determines for each $\theta$ the bandwidth scale factor $BWF(\theta)$ by the equation:

$$BWF(\theta) = [e^{(A_m(\theta) - A_o)} - 1] \cdot N_T / N_S \qquad (7).$$

It may be noted that Equation (7) guarantees that $BWF(\theta)$ is always greater than or equal to zero, i.e. assumes no negative values.

Looking to the missing view filter function selecting means 42, the regions with missing views can be considered as being undersampled with respect to the projection angle $\theta$. In fourth generation CT scanners, missing views generally correspond to bad detectors or detector modules. Accordingly, a formula for the bandwidth scale factor is readily determined given the number and location of the missing views. As an example for one missing view, the bandwidth scale factor of $2N_T/N_S$ satisfies the view sampling requirement for the extrapolated missing view; whereas, adjacent views would have a bandwidth selection factor of about $N_T/N_S$; and all other views (assuming no other missing views) would have a factor of zero, i.e. no filtering. Because the number of missing views is usually very small compared with the total number of views, view missing related artifacts are eliminated with no measurable impact on resolution.

The high density object bandwidth filter selecting means 44 in a simplest case may change the bandwidth scale factor between zero as views through the patient's body are taken and a preselected value for views through the patient's arms. Alternately, the high density object bandwidth scaling factor may be selected dynamically in accordance with other criteria, such as size of the patient and patient's arms, degree of alignment between bone tissue in the arms and the cervical spine, alignment of other bone tissue with the spine or other regions of the patient to be imaged, compensation for other bone tissue adjacent regions of interest, and the like. In views which include a high density object outside of the imaged area, the high resolution and distance of the interfering object cause the view sampling criterion to be violated. The bandwidth scale factor is selected such that appropriate views within the given angular range and location of the interfering objects are filtered sufficiently that the filtered data meets the sampling criterion. This can be estimated in advance based on the type of scan being conducted or may be calculated from the currently collected data, data from the preceding adjoining slice, or the like.

The noise texture means 46 selects bandwidth correction factors which obtain a non-circularly symmetric point response function in the reconstructed image. Higher order noise statistics or texture can be altered without affecting the nominal noise and resolution measurements. For example, reducing the bandwidth at 45°, 135°, 225°, and 315° while maintaining full bandwidth at 0°, 90°, 180°, and 270° distorts a normally circular noise texture by drawing it out at the corners (45°, 135°, 225°, and 315°) and holding it in at midpoints (0°, 90°, 180°, 270°) to approximate a square or rectangle. A suitable bandwidth factor for achieving this noise texture correction is:

$$BWF(\theta) = (N_T/N_S) \cdot \sqrt{(1 + \sin^2(2\theta))} \qquad (8).$$

When a circularly symmetric reconstruction kernel is used in the reconstruction means 30, the filter function of Equation (8) gives an asymmetric point response that is generally rectangular in form whose nominal response, measured over 360° is comparable to the original image. A response of this nature may be particularly advantageous for imaging on a rectangular matrix.

Analogously, other view dependent bandwidth scaling factors can be selected. The bandwidth scaling factor selecting means 50 selects among the bandwidth factors generated by each of the bandwidth factor selecting means 40–48. In the preferred embodiment, the selected bandwidth scaling factor $BWF(\theta)$ is the maximum value among the generated bandwidth functions, i.e.:

$$BWF(\theta) = MAX[BWF_{adaptive}(\theta), BWF_{missing\ views}(\theta), BWF_{object}(\theta), BWF_{asymm}(\theta)] \qquad (9).$$

In this manner, a single bandwidth scale factor as a function of the view designation $\theta$ is provided.

The invention has been described with reference to the preferred embodiments. It is intended that the invention be construed as including all such alterations and modifications insofar as they come within the scope of the appended claims or the equivalents thereof.

Having thus described the preferred embodiment, the invention is now claimed to be:

1. A diagnostic imaging apparatus comprising:
    a scanner for generating a plurality of views for reconstruction into an image representation of an examined subject, each view including a set of data corresponding to a different angular orientation around the subject, each view being identified by a corresponding view identification, the view identification being identifying the angular orientation corresponding to the data set of each view;
    a filter-function providing means for providing a plurality of filter functions for each view in accordance with the view identification, at least one or more of the filter functions changing from view to view;
    a filter control means operatively connected with the scanner to receive the view identification of each view and with the filter function providing means for dynamically selecting one of the plurality of filter functions provided in accordance with each received view identification;
    a filter means operatively connected with the scanner and the filter control means to receive concurrently each view and the one of the plurality of filter functions selected for the received view for filtering each received view with the filter function selected for the each received view;
    a reconstruction means operatively connected with the filter means for reconstructing an image representation from the filtered views.

2. A diagnostic imaging apparatus comprising:
    a scanner for generating a plurality of views for reconstruction into an image representation;

a filter control means for dynamically selecting at least one of a bandwidth scaling factor and a bandwidth offset for each generated view;

a filter function look up table which is addressed by the selected at least one of the bandwidth scaling factor and the bandwidth offset from the filter control means to retrieve a corresponding one of a plurality of filter functions the filter function look-up table being connected with the filter control means;

a filter means for filtering each view with the retrieved filter functions, the filter means being operatively connected with the scanner and the filter function look up table;

a reconstruction means for reconstructing an image representation from the filtered views, the reconstruction means being connected with the filter means.

3. The apparatus as set forth in claim 2 wherein each view has a first plurality of digital data values and the filter functions stored by the filter function look up table have a smaller plurality of digital filter values and further including an interpolating means for interpolating the filter values such that the filter function has the same number of digital values as each view, the interpolating means being operatively connected with the filter means.

4. The apparatus as set forth in claim 3 wherein the filter means includes a multiplying means for multiplying the interpolated filter values and the data values point by point.

5. The apparatus as set forth in claim 2 wherein the filter control means includes at least one of:

a noise filter providing means for providing bandwidth scaling factors for compensating for noise;

a missing view filter providing means for providing bandwidth scaling factors to compensate for missing views;

a noise texture filter providing means for providing bandwidth scaling factors for adjusting noise texture.

6. The apparatus as set forth in claim 2 wherein the filter control means includes a plurality of bandwidth filter function providing means for providing a plurality of bandwidth scaling factors for each view, the bandwidth scaling factors varying from view to view.

7. The apparatus as set forth in claim 7 wherein the bandwidth filter function providing means include at least two of:

a noise filter providing means for providing a view dependent bandwidth scaling factor for compensating for noise;

a missing view filter providing means for providing bandwidth scaling factors to compensate for missing views;

a noise texture filter means for providing a bandwidth scaling factor for adjusting noise texture;

a means for providing an out of region of interest material bandwidth scaling factor which adjusts the bandwidth of selected views to accommodate material adjacent an imaged region of interest.

8. A diagnostic imaging apparatus comprising:

a scanner for generating patient data including a plurality of views for reconstruction into an image representation of an imaged region;

a filter selecting means for selecting one of a plurality of filter functions, the filter functions including at least two of (i) a noise filter, (ii) a view dependent adjacent high density material filter which compensates for high density structures adjacent the imaged region, (iii) a view dependent noise texture filter, and (iv) a missing view filter function for weighting views interpolated to replace missing views and views adjoining the missing views;

a filter means for operating on each view with the selected filter function;

a reconstruction means for reconstructing an image representation from the filtered views.

9. A method of generating an image representation, the method comprising:

non-invasively examining an interior portion of a subject within an examination region and generating patient data including a plurality of views indicative thereof for reconstruction into an image representation of the examined region;

providing an identification of each view;

receiving each provided identification and providing a plurality of corresponding view dependent filter functions for each view such that the plurality of provided filter functions varies from view to view;

in response to each view identification, selecting one of the plurality of provided filter functions;

filtering each view with the selected one of the plurality of provided filter functions;

reconstructing the filtered views into the image representation.

10. A method of generating an image representation, the method comprising:

non-invasively examining an interior portion of a subject within an examination region and generating patient data including a plurality of views indicative thereof for reconstruction into an image representation of the examined region;

storing at least one of a bandwidth scaling factor and a bandwidth offset for each view;

addressing a filter function look up table with the one of the bandwidth scaling factor and offset to retrieve a corresponding filter function therefrom;

operating on the patient data with the addressed filter function of the corresponding view;

reconstructing the views which have been operated on by the addressed filter function into the image representation.

11. The method as set forth in claim 10 further including:

storing a plurality of bandwidth scaling factors for each view; and, comparing the plurality of bandwidth scaling factors with a preselected criterion and selecting one of the bandwidth scaling factors to address the look up table in accordance with the comparing.

12. The method as set forth in claim 16 wherein the plurality of bandwidth scaling factors compensate for at least two of noise, missing views, material surrounding the region of interest, and noise texture.

13. A method of generating an image representation, the method comprising:

non-invasively examining an interior portion of a subject within an examination region and generating patient data including a plurality of views indicative thereof for reconstruction into an image representation of the examined region;

selecting a filter function for each view from among a plurality of filter functions including at least two of:

a noise filter function for correcting for noise, a missing views filter function for correcting for missing views, a surrounding material filter function for correcting for material surrounding the region of interest, and a noise texture filter function for correcting for noise texture;

operating on each view the patient data with the selected filter function selected for that view;

reconstructing the filtered views into the image representation.

14. A diagnostic imaging apparatus comprising:

a scanner for generating a plurality of views, each view including a real component and an imaginary component;

a filter control means for dynamically selecting (i) one of a plurality of real bandwidth factors for each view and (ii) one of a plurality of imaginary bandwidth factors for each view, on a view-by-view basis;

a filter function look up table means which is addressed by the real and imaginary bandwidth factors to retrieve corresponding real and imaginary filter functions, the filter function look up table means being operatively connected with the filter control means;

a filter means for filtering the real component of each view with the retrieved real filter function and for filtering the imaginary component of each view with the retrieved imaginary filter function, the filter means being operatively connected with the scanner to receive the real and imaginary component of each view therefrom and with the filter function look up table means for receiving the retrieved real and imaginary filter functions therefrom; and a reconstruction means for reconstructing an image representation from the filtered real and imaginary components, the reconstruction means being operatively connected with the filter means to receive the filtered real and imaginary components therefrom.

* * * * *